United States Patent
Schmieding

(10) Patent No.: US 6,591,581 B2
(45) Date of Patent: Jul. 15, 2003

(54) METHOD FOR PREPARING AND INSERTING ROUND, SIZE SPECIFIC OSTEOCHONDRAL CORES IN THE KNEE

(75) Inventor: Reinhold Schmieding, Naples, FL (US)

(73) Assignee: Arthrex, Inc., Naples, FL (US)

(*) Notice: Subject to any disclaimer, the term of this patent is extended or adjusted under 35 U.S.C. 154(b) by 75 days.

(21) Appl. No.: 09/800,485

(22) Filed: Mar. 8, 2001

(65) Prior Publication Data
US 2002/0157676 A1 Oct. 31, 2002

Related U.S. Application Data
(60) Provisional application No. 60/187,877, filed on Mar. 8, 2000.

(51) Int. Cl.$^7$ ............................................... A61B 17/56
(52) U.S. Cl. ..................... 53/396; 128/898; 700/213; 623/11.11; 623/16.11; 623/23.61; 623/908
(58) Field of Search ........................ 53/396; 128/898; 623/11.11, 16.11, 23.51, 23.61, 23.72, 23.75, 902, 908; 700/213; 705/2

(56) References Cited

U.S. PATENT DOCUMENTS

| | | | | |
|---|---|---|---|---|
| 4,486,188 A | * | 12/1984 | Altshuler et al. | 604/38 |
| 5,549,675 A | * | 8/1996 | Neuenfeldt et al. | 424/93.7 |
| 5,919,196 A | * | 7/1999 | Bobic et al. | 606/86 |
| 6,029,422 A | * | 2/2000 | Alt | 53/425 |
| 6,364,907 B1 | * | 4/2002 | Obochi et al. | 128/898 |

* cited by examiner

Primary Examiner—Stephen F. Gerrity
Assistant Examiner—Brian D Nash
(74) Attorney, Agent, or Firm—Dickstein Shapiro Morin & Oshinsky, LLP

(57) ABSTRACT

In a method of performing a hyaline cartilage allograft transplantation procedure in which a surgeon has pre-operatively determined a size of allograft to be needed for the procedure, a service provider facilitates the procedure by arranging, upon receiving an order from the surgeon or a hospital for an allograft of a specified diameter, for the delivery of a precut allograft core along with a customized set of instrumentation for performing the transplantation to the surgeon or hospital prior to the scheduled time of the operation. The service provider also arranges for the return of any non-disposable instrumentation to the service provider after the operation.

14 Claims, 7 Drawing Sheets

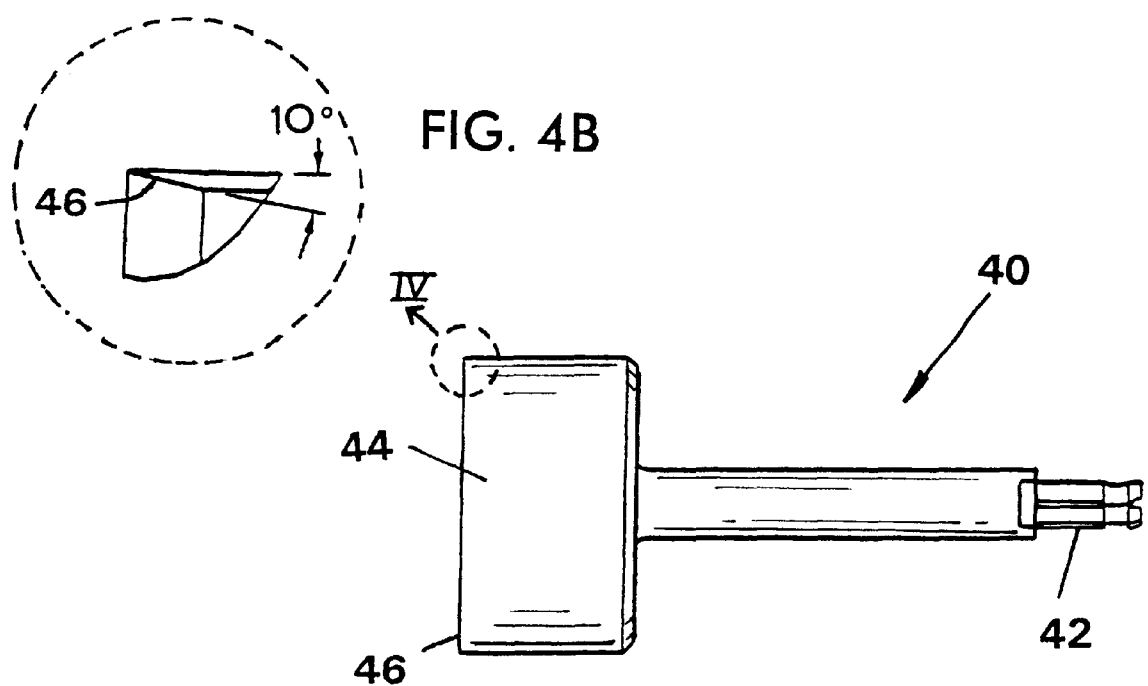
FIG. 4B
FIG. 4A
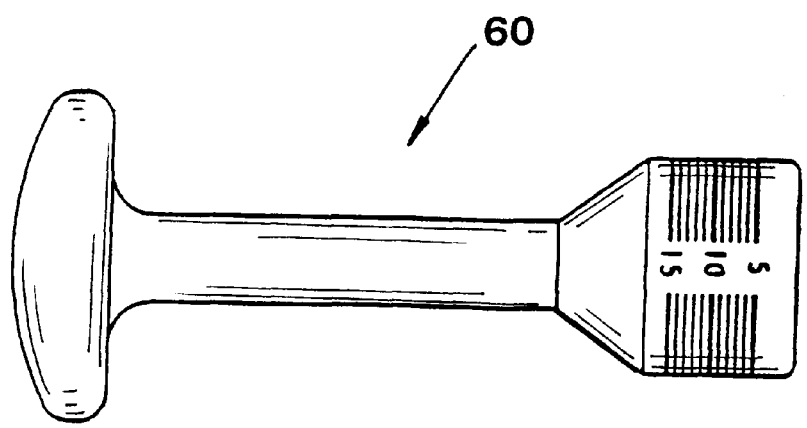
FIG. 6

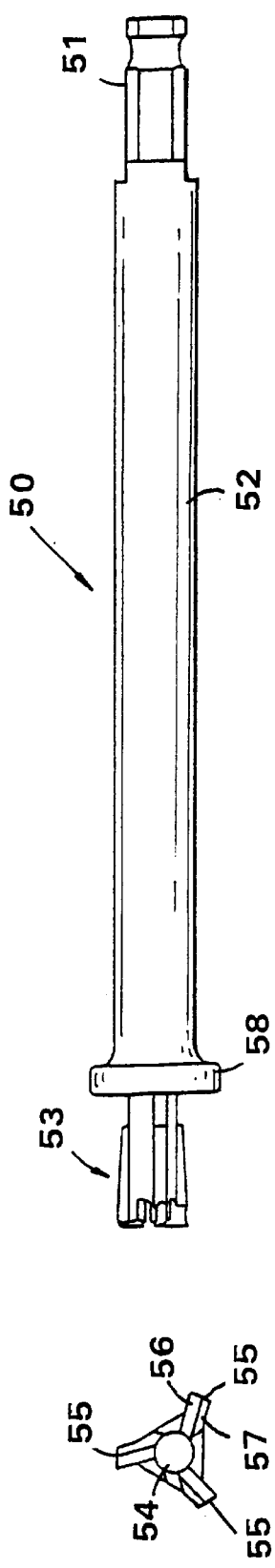
FIG. 5A
FIG. 5B
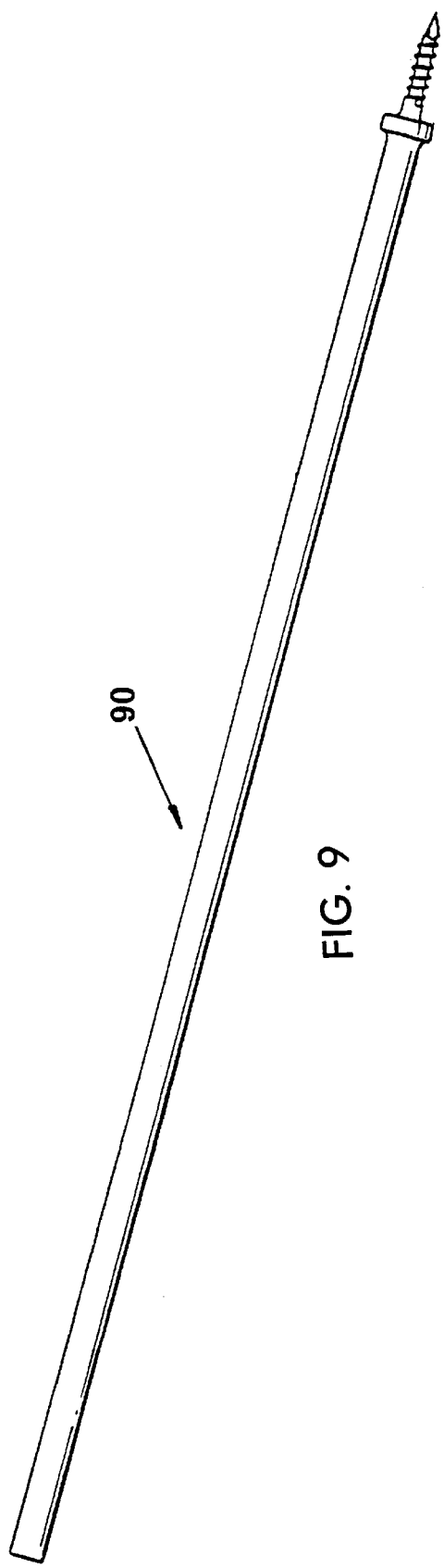
FIG. 9

METHOD FOR PREPARING AND INSERTING ROUND, SIZE SPECIFIC OSTEOCHONDRAL CORES IN THE KNEE

This application claims the benefit of U.S. Provisional Patent Application Serial No. 60/187,877, filed on Mar. 8, 2000.

BACKGROUND OF THE INVENTION

1. Field of the Invention

The present invention relates to the surgical treatment of isolated articular chondral defects and, more specifically, to methods and instruments for allograft transplantation of articular cartilage in the knee using round, size specific fresh hyaline cartilage grafts.

2. Description of the Related Art

Chondral defects, i.e. defective cartilage, of the femoral condyles can vary from superficial blemishes and fissures, to large, full-thickness defects. These lesions may also occur as isolated pathology in cruciate normal knees. In the past, however, treatment has been difficult and controversial. Thus, in many earlier known methods, other indications in the knee would be treated, but the chondral lesion usually was left untreated. This approach leads to lesion enlargement and ultimately an advancing arthritic condition.

More recently, chondral defects of the femoral condyles have become widely recognized indications which comprise approximately 5% of all knees undergoing arthroscopy. As such, chondral defects in the knee are typically treated by autograft transplantation of bone cores in the knee, as described in U.S. Pat. No. 5,919,196, the disclosure of which is hereby incorporated by reference. However, autografts cause additional intervention surgery, increased pain and infusion, and only provide a maximum of 2 or 3 cores to treat smaller focal defects. Furthermore, the donor core must be taken from a location different from the recipient site, thus preventing a perfect match in curvature of the cartilage surface.

As an alternative to the above-described autograft method of treating focal osteochondral defects, an allograft osteochondral transplantation method is known, in which a surgeon is provided with a whole cadaver knee from a tissue bank, along with an instrument set containing the full range of sizers and sized instruments. In this allograft method, the surgeon must determine the size of the graft needed and then harvest the properly sized allografts at the time and location of performing the surgery. This method is undesirable, however, due to several factors, including the preoperative preparation required for the surgeon to harvest and prepare the donor core, the waste from discarding each cadaver knee after the one operation without realizing the full potential for each knee to yield multiple allograft cores, and the comprehensive instrumentation system which must be sent to and recovered from the operation site.

Moreover, many times the surgeon will determine the presence of a chondral defect during treatment of another condition, and must schedule another surgery to repair the chondral defect. In such instances or in other situations when the surgeon is able to determine the size of the defect prior to the time of the scheduled surgery to repair the chondral defect, the surgery would be much less time-consuming and less burdensome on the surgeon if the surgeon could obtain an appropriately sized, ready-to-use donor graft, prior to the start of the surgery on the patient.

Accordingly, it would be desirable to provide a method of repairing chondral defects using allograft cores which are precut to the correct size and prepared for transplantation using corresponding instruments.

SUMMARY OF THE INVENTION

A first aspect of the present invention is to provide a service which significantly reduces the amount of work to be performed by a surgeon during a bone core transplantation surgery.

A second aspect of the present invention is to provide a streamlined and cost-effective service to facilitate the performance of an allograft core transplantation surgery.

A third aspect of the present invention is to arrange for the delivery of a precut allograft core to a surgeon or hospital prior to the performance of a transplantation surgery.

The present invention comprises a method for facilitating a hyaline cartilage allograft transplantation procedure in which a service provider, upon receiving an order for an allograft of a specified diameter, arranges for the delivery of a precut allograft core along with a customized set of instrumentation for performing the transplantation to the operation location prior to the scheduled time of the operation. The service provider also arranges for the return of any non-disposable instrumentation to the service provider after the operation.

Other features and advantages of the present invention will become apparent from the following description of the invention which refers to the accompanying drawings.

BRIEF DESCRIPTION OF THE DRAWINGS

FIG. 4A shows a recipient cutter tube usable in connection with the method of the present invention.

FIG. 4B shows an enlargement of a cross section of the area IV showing a beveled edge of the cutter tube of FIG. 4A.

FIG. 5A shows a counterbore drill tip in accordance with the present invention.

FIG. 5B shows a distal view of the drill tip of FIG. 5A.

FIG. 6 shows a dilator used in connection with the method of the present invention.

FIG. 9 shows a graft retriever usable in connection with the method of the present invention.

DETAILED DESCRIPTION OF THE PREFERRED EMBODIMENTS

Figure 1:
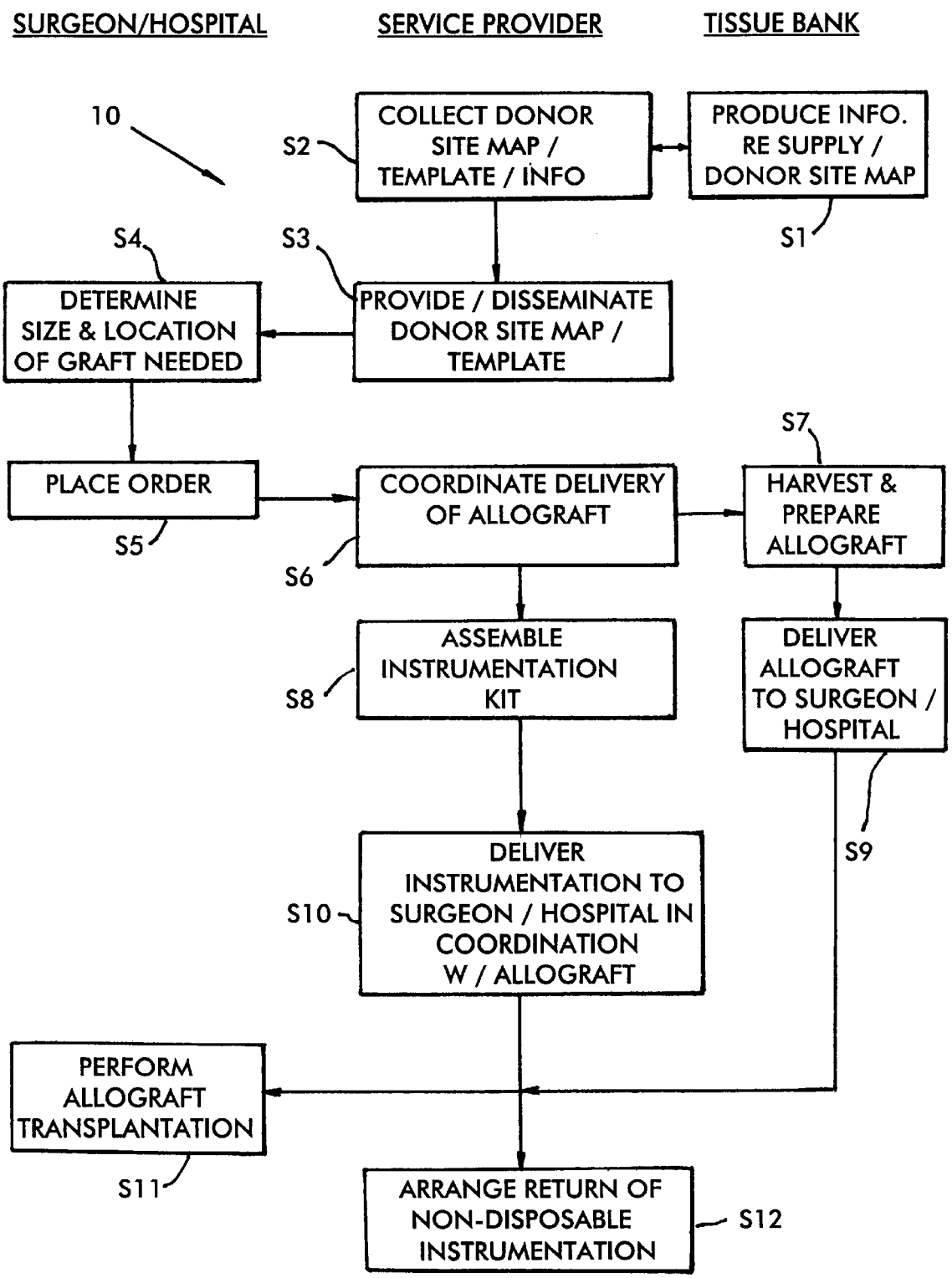
FIG. 1 is a diagrammatic outline of the method according to the present invention.

The method of the present invention 10 is diagrammatically outlined in FIG. 1. In this method, a service provider coordinates the delivery of a precut allograft core from a tissue bank, e.g., the University of Miami Tissue Bank, and a customized instrumentation kit to a surgeon's office or hospital for a bone core transplantation operation.

Figure 2:
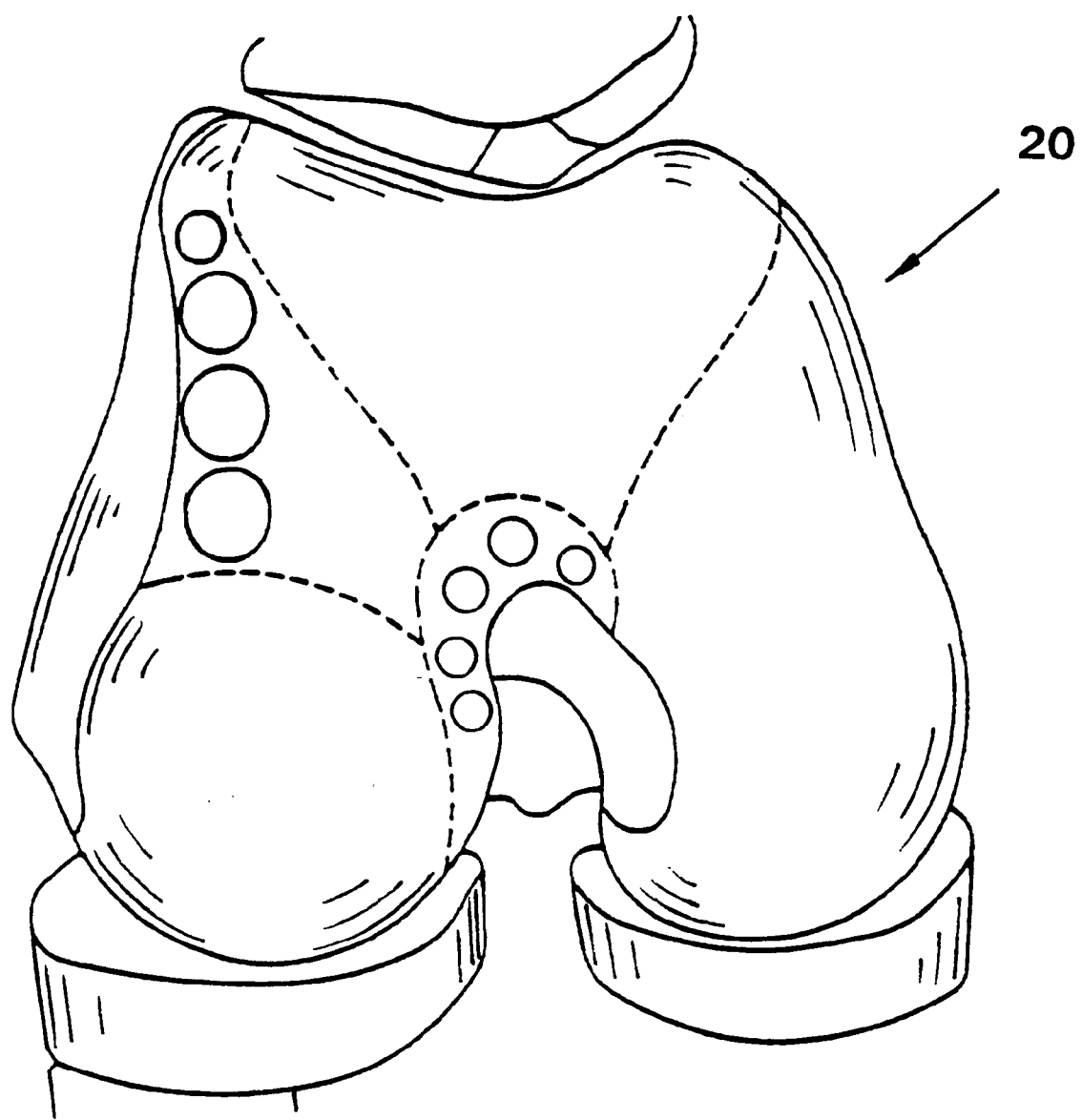
FIG. 2. is an example of several template or mapped donor sites to be provided to a practitioner for facilitating an order for an allograft core in accordance with the present invention.

In step S1 shown in FIG. 1, the tissue bank maps the harvest locations of the donor femur to provide a visual indication of the area and shape of the cartilage of the knee from which the donor core is to be harvested. This mapping consists of a photograph of the donor's distal femur with donor sites marked with reference numbers for identification. The service provider collects and compiles the donor site information as well as information regarding the availability of allograft cores from a plurality of tissue banks (step S2). Alternatively, the participating tissue banks and the service provider may adhere to a standard template for mapping the donor sites on a cadaver knee available for harvesting. FIG. 2 shows an example of a template 20 showing several potential donor sites in a knee having different diameters and different curvatures, which may serve as the basis for a donor site map or template.

In step S3, the service provider disseminates the donor site map or template information to practitioners and/or potential clients, either upon request in anticipation of receiving an order or as part of marketing literature. Using the donor site or template information, the surgeon can identify the appropriate cartilage thickness and curvature to match the requirements of the size and position of the chondral defect on the femoral condyle being treated prior to ordering the grafts (step S4). The surgeon can then perfectly select the allograft core that fits the needs of the patient with a defect in the same area and cartilage shape. Typically, allograft cores can be specified to have either a convex or concave cartilage surface, and a diameter ranging from about 8 mm to about 20 mm, in 2 mm increments.

In a preferred embodiment of the present invention, the surgeon or hospital places the order for the allograft through the service provider (step S5), who then notifies the appropriate tissue bank (step S6), and coordinates the delivery of the allograft with the assembly and delivery of a customized set of instrumentation for the specific procedure (steps S8, S10), as well as arranges for any training which may be necessary for the surgeon.

After an order is placed by the surgeon, the tissue bank harvests the graft within the designated time frame prior to the scheduled surgery (step S7). To harvest the donor core, a coring trephine with teeth is preferably used, which has an inner diameter between 0.5 mm to 0.1 mm undersized of the socket created in the recipient knee. Bone cores with hyaline cartilage are harvested in approximately 7.9 mm, 9.9 mm, 11.9 mm, etc. diameters. Alternatively, a donor harvester having a straight cutting edge such as that disclosed in U.S. Pat. No. 5,919,196 may be used.

As the core is removed from the donor site, the 12 o'clock position in relation to the position in which it was harvested from the knee is marked with methylene blue. This provides the surgeon with an identification of the proper rotational orientation of the cartilage when the allograft is inserted into the recipient socket. Photographs are taken by the tissue bank to document the site of harvesting from the donor knee and the final shape of the graft from a frontal and cross sectional view. The allograft is tested by the tissue bank for any potential transmittable diseases (HIV, hepatitis, etc.), and to ensure that the tissue is healthy. If needed, the core may be cut or shaped. After documentation and testing, the prepared core is packaged and cooled fresh, without freezing or freeze dried preservation technique.

Preferably, upon packaging the precut core for delivery to the surgeon or hospital, the tissue bank inserts the allograft core into a clear or translucent plastic delivery tube as described below, with the cartilage end in first, so that the core and the delivery tube are packaged as a unit. Alternatively, the allograft may be packaged separately and the delivery tube may be provided with the other tools to be mentioned later.

Figure 3A:
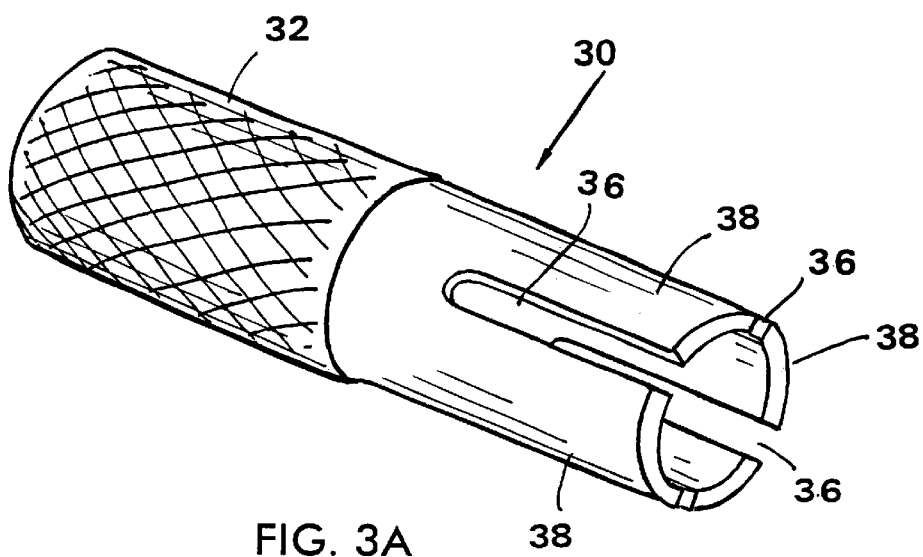
FIG. 3A is a perspective view of a delivery tube in accordance with the present invention.
Figure 3B:
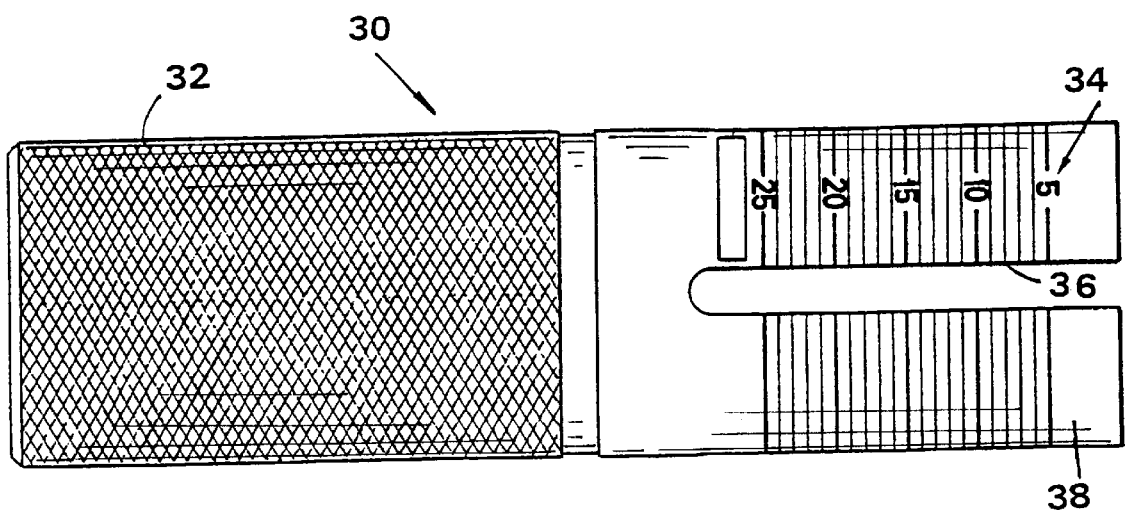
FIG. 3B is a side elevational view of the delivery tube in accordance with the present invention.

Delivery tube 30 is illustrated in FIGS. 3A and 3B, and is approximately 3–4 inches in length and made from a clear or translucent plastic material. The proximal portion of the tube, approximately half the length, preferably has a knurled exterior surface 32 to facilitate grasping of the tube during an insertion procedure. The distal portion may include graduated markings 34 etched onto the surface for indicating a depth or length of a core inserted therein. As shown in FIG. 3B, for example, the markings indicate a range of from 5 mm to 25 mm.

The distal portion of delivery tube 30 has at least two, and preferably four, axially extending slots 36 having a width of approximately 3 mm and a length of approximately one-third the length of the tube. The inside diameter of the tube can be the same diameter as the allograft core and is constant along the entire length of the tube. Alternatively, the inside diameter of the tube can be slightly greater than the core diameter along most of the tube while slightly tapering from the proximal end of the slots to the distal end, with the distal end having a decreased diameter with respect to the proximal portion. Distal "fingers" 38 are formed between the axial slots which expand slightly to securely grip the core when inserted therebetween.

To accommodate a wide range of allograft sizes, a plurality of delivery tubes are available to the tissue bank corresponding with different sized diameters of the allografts to be harvested. The delivery tubes may be provided to be single-use and disposable, or alternatively, reusable. If the delivery tube is provided to be disposable, either or both the knurled proximal surface and the distal scale markings may be omitted.

Shortly before the operation date, the allograft core is packaged as discussed above and shipped to the surgeon or hospital in a cooled packaging (step S9). The timing of the delivery to the surgeon is important because a fresh graft such as the precut allograft core of the present invention must be used within 14 days to retain live hyaline cartilage cell life.

The service provider coordinates the delivery of the graft to the hospital or surgeon's office with a simultaneous or temporally proximal delivery of the instrumentation needed by the surgeon to perform the transplantation (step S10). Preferably, the instruments are owned by the service provider and are loaned to the surgeon or hospital for the transplantation. Alternatively, the service provider may arrange for the instruments to be sent to the surgeon or hospital from another provider.

As mentioned above, the allograft may be packaged alone or pre-inserted into the delivery tube prior to delivery of the allograft to the surgeon or hospital. If the allograft is packaged alone, a delivery tube is provided with the instrumentation package delivered separately to the site of the operation. Such instrumentation includes a recipient cutting tube 40 (FIG. 4A), a counterbore drill tip 50 (FIG. 5A), a guide pin, a quick-connect drive handle and associated parts (i.e., adapters), a dilator 60 (FIG. 6), a delivery sizer 70 (FIG. 7A), a tamp 80 (FIG. 8A), a graft retriever 90 (FIG. 9), a tunnel measurement guide, and holding forceps. The delivery tube, drill tip, cutting tube, delivery sizer and bore dilator are selected by the service provider to correspond with the diameter of the allograft core ordered by practitioner and delivered by the tissue bank.

To transplant the bone core, the surgeon must prepare the recipient site by removing bone material to form a socket corresponding in diameter or slightly larger than (by about 0.5 mm) the diameter of the allograft core. Using the cutting tube 40 and the counterbore drill tip 50, the surgeon creates the sized recipient socket corresponding to the focal defect and the allograft core used to replace the bone and cartilage surface to match the surrounding cartilage in the knee.

As shown in FIG. 4, the cutting tube 40 has a proximal end 42 designed to be releasably engaged with the quick-connect handle and has an a cylindrical cutting portion 44 at the distal end. The cylindrical cutting portion has a circumferential beveled cutting edge similar to the recipient harvester disclosed in U.S. Pat. No. 5,919,196. The cutting tube is used to define the location of the hole to be drilled so as to encompass the defective area, and to create a clean socket circumference along at least the upper portion of the hole to be drilled. The inside diameter of the starter is sized to define a hole of 8, 10, 12, 14 mm, etc. in diameter. In use, the cutting tube functions similarly to a cookie cutter and is driven into the bone by impacting the drive handle with a mallet as is known in the art or by rotating it with the drive handle.

After defining the outline of the recipient socket with the cutting tube, the interior of the socket is drilled out using the counterbore drill tip 50 shown in FIGS. 5A and 5B. The drill tip as provided by the service provider is sized to drill a hole of 8, 10, 12, 14 mm, etc. in diameter in accordance with the diameter of the cutting tube, and to a depth of approximately 12 mm. The drill tip 50 has a proximal end 51 constructed to be releasably engaged with a chuck in the quick-connect handle, a shaft body 52, and a cutter portion 53 at the distal portion of the drill tip. A central cannula 54 extends along the length of the drill tip from an opening at the proximal end to an opening at the distal end thereof to receive insertion of a guide pin therethrough to facilitate proper alignment within the area defined by the cutting tube during drilling of the recipient socket.

The distal portion of the drill tip has a substantially triangular cross section and forms three cutter edges 55 equally spaced around the central cannula. The three cutter edges do not radiate along radial lines, but are "folded" slightly counterclockwise so that the radially outermost end of each edge is positioned "ahead" of the radially innermost end of the respective edge in the counterclockwise direction. Each cutter edge 55 is beveled along both the leading face 56 and the trailing face 57 thereof, with the leading face 56 undercut to a steeper degree than the relief cut of the trailing face 57. Such design makes the cutter edge sharper than the four-edged drill tip used in the prior art allograft transplantation method. Additionally, the relief cut at the trailing face of each cutter edge enhances the cutting ability by facilitating the evacuation of debris from the hole as it is being drilled.

The base of the shaft body 52 expands radially to form a circumferential flange 58 proximally to the cutter portion. The flange is positioned approximately 12 mm from the distal end of the cutter edges and has a diameter wider than the cutter portion to serve as a depth stop. During drilling, when the distal surface of the depth stop contacts the cartilage surface of the recipient site, the hole has been drilled to approximately a desired depth, and the surgeon is prevented from drilling too deeply into the patient's bone without causing damage to the surrounding bone surface. Using the drill tip of the present invention, preparation of the recipient socket for receiving the allograft core can be performed more easily and more quickly than in the past.

The dilator 60 shown in FIG. 6 is used to complete the socket by slightly compacting the socket wall and floor to prepare the seating surfaces for receiving the transplanted core. A flat ended alignment stick or tunnel measurement stick is used to measure precisely the socket depth, generally in the range of about 12–15 mm. If necessary, "fine-tuning" adjustments such as trimming the length of the donor core and shaping the bottom face may be performed to ensure proper seating of the donor core in the recipient socket. The forceps provided with the instrumentation set are used to handle the allograft, or the core is held between the "fingers" 38 formed by the axial slots 36 at the distal portion of the delivery tube 30.

Figure 7A:
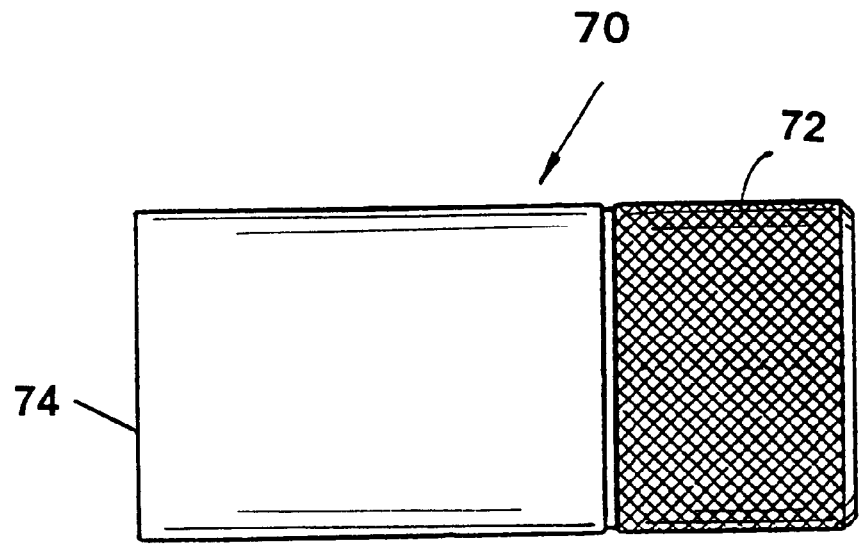
FIG. 7A is a side view of a delivery sizer in accordance with the present invention.
Figure 7B:
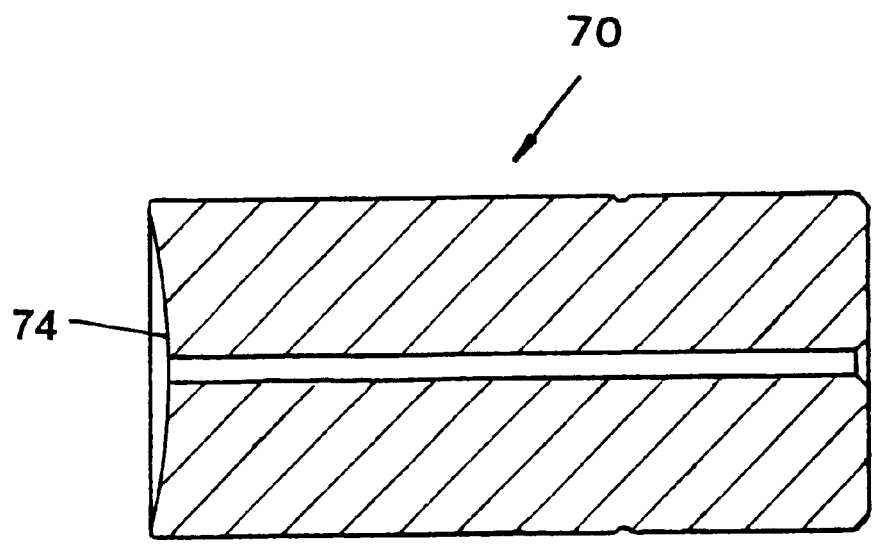
FIG. 7B is a cross-sectional view of the delivery sizer shown in FIG. 7A.

After preparation of the recipient socket and any necessary fine-tuning of the allograft core, the surgeon transfers the donor core to the prepared site (step S11). If the allograft is delivered to the surgeon outside of the delivery tube, the allograft is placed into the proximal end of the delivery tube 30 or inserted from the distal end with the cartilage end facing up (proximally). A delivery sizer 70 shown in FIGS. 7A and 7B is used to push the allograft down the delivery tube until the core is grasped within the "fingers" between the axial slots. For this purpose, sizer 70 has an outer diameter slightly smaller than the inner diameter of the delivery tube and a length approximately the same length as the delivery tube. The proximal end 72 of the sizer is preferably knurled in a similar manner to the proximal end of the delivery tube to protect against slippage when grasping the sizer. The distal face 74 of the sizer is slightly concave with a spherical curvature to accommodate the naturally convex curvature of the cartilage surface of the allograft core. As with the delivery tube, the sizer 70 may be formed without the knurled proximal surface, especially if the sizer is provided to be disposable.

Figure 8A:
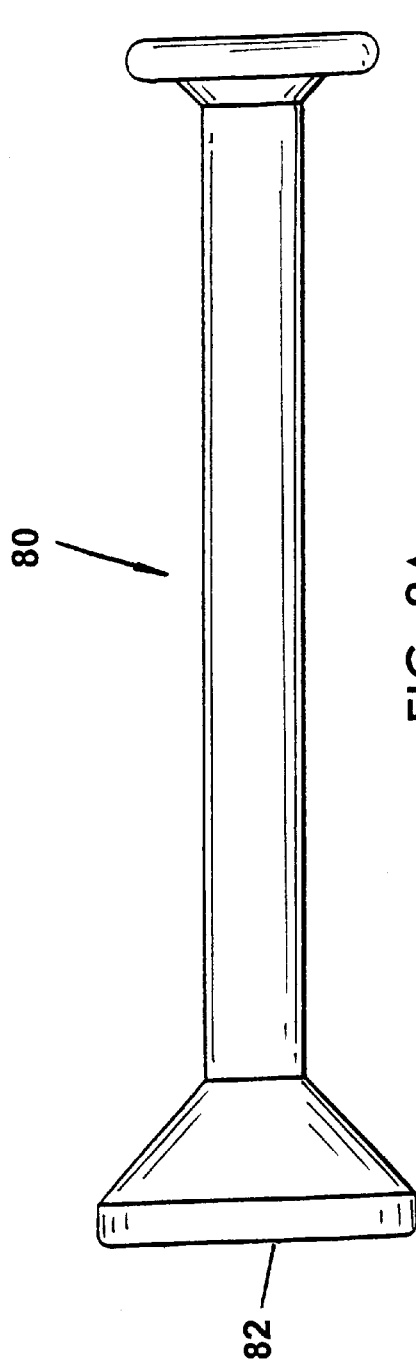
FIG. 8A is a side view of a tamp usable in accordance with the method of the present invention.
Figure 8B:
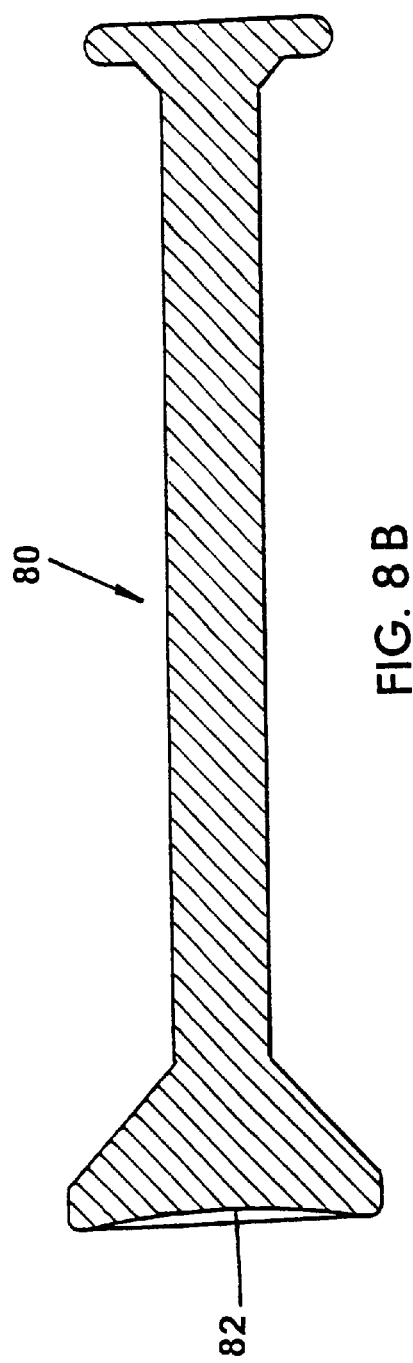
FIG. 8B is a cross-sectional view of the tamp shown in FIG. 8A.

The allograft core is transplanted to the recipient socket by placing the periphery of the distal tube end around the socket opening to stabilize the delivery angle. The clear/translucent delivery tube allows visibility within, and functions as a stabilizer and alignment guide during transplantation. Taking care to align the methylene blue mark on the allograft core with the 12 o'clock position of the recipient socket, the sizer is used to push the core out of the delivery tube and into the socket. Typically, the core is inserted into the socket until the surface of the core is still about 1 mm proud of the surface of the surrounding bone tissue, whereupon a tamp 80 shown in FIGS. 8A and 8B is used to insert the core the final distance until the core surface is flush with the surface of the surrounding bone tissue. The tamp is used for the final delivery because the distal face 82 thereof has a diameter, or at least a width which is wider than the diameter of the core, and, like the distal face of the delivery sizer, is slightly concave. Since the distal face of the tamp is wider than the core, over-insertion or compression damage to the core can be avoided.

In the event that the donor core must be removed from the recipient socket at any time during or after insertion, for example if insertion was started at an inappropriate angle or if the core was inserted too deeply so as to leave a depression at the transplant site, the graft retriever 90 shown in FIG. 9 can be used to back the core out of the socket. The slightly undersized donor core enables it to be easily extracted from the tube into the recipient socket, if necessary, with minimal compression forces that might otherwise damage the pressure sensitive chondrocytes of the cartilage surface.

Grafts with concave hyaline cartilage surfaces are harvested at the tissue bank in the same manner described above for replacing diseased cartilage in the knee with corresponding concave surfaces. The transplantation procedure is identical, except that the delivery sizer and tamp provided to the surgeon would have a convex, rather than a concave, distal surface.

After the transplantation surgery, the service provider arranges for the return of any non-disposable instrumentation (step S12). Optionally, some or all of the instruments provided to the practitioner may be disposable, thus eliminating the need to arrange for their return to the service provider and for resterilization of the instruments between shipments.

Advantageously, in accordance with the present invention, the allograft cores are harvested in a sterile surgical environment by the tissue bank, and are tested and prepared in special containers for shipment to the patient's hospital in a cooled environment to preserve the fresh bone and cartilage for transplantation within 14 days. In contrast to conventional autograft surgery, the present invention provides a greater source of transplantation material while also avoiding the additional surgery required to harvest an autograft.

Other advantages realized by the present invention include less waste of the donor tissue, as one cadaver knee could be harvested to provide allografts for several transplantation operations at different locations and by different hospitals and surgeons, and the elimination of shipment to and from the operation site of surplus instrumentation not needed or used to perform the operation.

Of course, in situations where the size of the chondral defect cannot be determined beforehand or where the surgeon desires the security of being able to harvest additional cores in the event the initial core becomes damaged or spoiled due to error or inexperience, it will be necessary for the surgeon or hospital to use the traditional allograft method so that the fill range of instruments in all the sizes is available to the surgeon at the time of operation.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A method for allograft bone core transplantation, comprising the step of:
    placing an order for a precut allograft core by a surgeon to a core provider, the precut allograft core having a specified diameter; and
    delivering the precut allograft core having the specified diameter from the core provider to the surgeon prior to a scheduled transplantation operation.

2. The method according to claim 1, wherein the precut allograft core is inserted into a clear or translucent delivery tube prior to packaging for delivery to the surgeon.

3. The method according to claim 1, further comprising:
    assembling a customized instrumentation set for the transplantation operation of the precut core having the specified diameter; and
    providing the customized instrumentation set simultaneously with or temporally proximate to the delivery of the precut allograft core to the surgeon prior to the scheduled operation.

4. A method for allograft bone core transplantation, comprising the step of:
    delivering, from a core provider to a surgeon, prior to a scheduled transplantation operation, a precut allograft core having a specified diameter; and
    providing for the return of at least one instrument of the customized instrumentation set to the originating location after performance of the transplantation operation.

5. The method according to claim 3, wherein at least some of the equipment in the customized instrumentation set is disposable.

6. A method for allograft bone core transplantation, comprising the step of:
    providing donor site identifying information to surgeons or hospitals assisting surgeons in identifying a size and curvature of an allograft core needed to perform the transplantation operation;
    receiving an order from a surgeon for the allograft core having a specified diameter based on the identifying information; and
    delivering the precut allograft core of the specified diameter, from a core provider to the surgeon, prior to a scheduled transplantation operation.

7. The method according to claim 6, wherein the donor site identifying information is a map of donor sites available for harvesting from a donor bone.

8. The method according to claim 6, wherein the donor site identifying information is compiled into a donor site map for locating a donor site harversting site from a donor bone.

9. A method for osteochondral bone core transplantation, comprising the step of:
    placing an order for a preformed osteochondral core by a surgeon to an external source, the preformed osteochondral core having a specified diameter; and
    delivering from the external source to the surgeon, prior to a scheduled transplantation operation, the preformed osteochondral core having the specified diameter.

10. The method according to claim 9, wherein the preformed osteochondral core is inserted into a clear or translucent delivery tube prior to packaging for delivery to the surgeon.

11. The method according to claim 9, further comprising:
    assembling a customized instrumentation set for the transplantation operation of the preformed core having the specified diameter; and
    providing the customized instrumentation set simultaneously with or temporally proximate to the delivery of the preformed osteochondral core to the surgeon prior to the scheduled operation.

12. The method according to claim 11, further comprising:
    returning at least one instrument of the customized instrumentation set to the originating location after performance of the transplantation operation.

13. The method according to claim 11, wherein at least one instrument of the customized instrumentation set is disposable.

14. A method for osteochondral bone core transplantation, comprising the step of:
    providing donor site identifying information to surgeons or hospitals assisting surgeons in identifying a size and curvature of a preformed osteochondral core needed to perform the transplantation operation;
    receiving an order from a surgeon for the preformed core based on the identifying information; and
    providing from an external source to the surgeon the preformed osteochondral core having the specified diameter, prior to a scheduled transplantation operation.

* * * * *